(12) United States Patent
Emmerling et al.

(10) Patent No.: US 6,730,290 B2
(45) Date of Patent: May 4, 2004

(54) AEROSOL SPRAY

(75) Inventors: Winfried Emmerling, Tornesch (DE); Uwe Bergemann, Hamburg (DE); Anja Thammasiri, Hamburg (DE)

(73) Assignee: Hans Schwarzkopf GmbH & Co. KG, Hamburg (DE)

( * ) Notice: Subject to any disclaimer, the term of this patent is extended or adjusted under 35 U.S.C. 154(b) by 0 days.

(21) Appl. No.: 10/228,413

(22) Filed: Aug. 26, 2002

(65) Prior Publication Data

US 2003/0118516 A1 Jun. 26, 2003

Related U.S. Application Data

(60) Provisional application No. 60/314,802, filed on Aug. 24, 2001.

(51) Int. Cl.[7] .............................. A61K 7/00; A61K 9/00; A61K 7/06; A61K 7/075; A61K 7/08
(52) U.S. Cl. .................... 424/47; 424/70.1; 424/70.9; 424/70.22; 424/70.23; 424/70.31; 424/400; 424/401; 424/DIG. 1; 514/787
(58) Field of Search ................................. 424/400, 401, 424/47, 70.1, 70.9, 70.22, 70.23, 70.31, DIG. 1; 514/787

(56) References Cited

U.S. PATENT DOCUMENTS

| 3,330,730 A | | 7/1967 | Hernandez | |
|---|---|---|---|---|
| 3,929,492 A | * | 12/1975 | Chapman et al. | 106/3 |
| 4,520,008 A | * | 5/1985 | Ando et al. | 424/47 |
| 5,286,475 A | * | 2/1994 | Louvet et al. | 424/45 |
| 6,132,736 A | * | 10/2000 | Mellul et al. | 424/401 |
| 6,153,196 A | | 11/2000 | Kripp et al. | |
| 2002/0122811 A1 | | 9/2002 | Stein et al. | |
| 2003/0059377 A1 | * | 3/2003 | Riley | 424/47 |

FOREIGN PATENT DOCUMENTS

| DE | 200 22 542 U1 | | 1/2002 |
|---|---|---|---|
| EP | 194097 A1 | * | 9/1986 |
| EP | 0686388 A1 | | 12/1995 |
| EP | 0 868 898 A1 | | 10/1998 |
| FR | 2 677 369 | | 12/1992 |
| GB | 1298154 | | 11/1972 |
| JP | 57-2215 | | 1/1982 |
| JP | 61287973 A | * | 12/1986 |
| JP | 2000-239131 | | 9/2000 |
| WO | WO98/16188 | | 4/1998 |
| WO | WO02/02708 A1 | * | 1/2002 |

OTHER PUBLICATIONS

Hawley's Condensed Chemical Dictionary, 13th ed, 1997, pp. 121, 204, 217, 675.*
Patent Abstracts of Japan, vol. 2000, No. 12, Jan. 3, 2001.
Patent Abstracts of Japan, vol. 006, No. 057 (C–098), Apr. 14, 1982.
Ullmans Encyklopädie der technischen Chemie, 4th Edition, vol. 24, p. 3, le hand column, 1983.

* cited by examiner

*Primary Examiner*—Thurman K. Page
*Assistant Examiner*—Marina Lamm
(74) *Attorney, Agent, or Firm*—Stephen D. Harper; Gregory M. Hill

(57) ABSTRACT

A composition and method for treating keratinous fibers. The composition contains a wax component and is formulated as an aerosol spray. Other components in the composition are at least one emulsifier and at least one propellant.

13 Claims, No Drawings

AEROSOL SPRAY

CROSS REFERENCE TO RELATED APPLICATIONS

This application claims priority to U.S. Provisional application serial No. 60/314,802 filed Aug. 24, 2001.

BACKGROUND OF THE INVENTION

The invention relates to a preparation for treating keratinous fibers, in particular human hair, in the form of an aerosol spray and to the use of this preparation for treating keratinous fibers, in particular human hair.

Keratinous fibers, in particular human hair, are subjected to a large number of treatments nowadays. The treatments, which are used for permanent or temporary styling of the hair, play an important part. Temporary styling which should give a good hold without impairing the healthy appearance of the hair, for example its shine, may be achieved, for example, by hairsprays, hair waxes, blow-dried waves etc.

Hair sprays usually contain synthetic polymers as the styling component. Preparations containing a dissolved or dispersed polymer may be applied to the hair by means of propellant gases or by a pump mechanism. A satisfactorily uniform distribution of the polymer over the hair is generally achieved in the process; application from spray or pump containers is simple and clean.

As the styling component, hair waxes generally contain vegetable, animal or mineral waxes and are sold as solid formulations, generally in pots. For application these products are firstly rubbed in the hand and then distributed over the hair. These hair waxes based on natural raw materials produce a good hold of the hair, simultaneously conferring a strong shine. Nevertheless, commercially available hair waxes cannot yet completely satisfy the user's wish for simple application and easy distribution over the hair. Rubbing on the hand necessitates either the use of gloves or subsequent intensive cleaning of the hands to remove the greasy feel of product residues. Furthermore, very uniform distribution of the product over the hair may only be achieved with difficulty and is very time-consuming.

Finally, there are also so-called shine sprays on the market. These may convey a particular shine, in particular to human hair, owing to their content of vegetable, mineral and/or synthetic oils. As the conventional synthetic and natural film-forming substances in these oils are practically insoluble, these shine sprays have no styling properties. The possibility of incorporating film-forming substances into shine sprays with the aid of solvents, for example large amounts of ethanol, does not lead to satisfactory results, as the additional styling properties may only be achieved at the cost of a significantly worse shine and feel.

SUMMARY OF THE INVENTION

It has now surprisingly been found that the waxes used in hair waxes may also be formulated and used as aerosol sprays. The product may therefore be applied to the hair much more easily and uniformly than conventional solid formulations. Furthermore there were no problems with respect to blockage of the nozzle by the wax components even when the spray cans were completely emptied. The problem of "greasy hands" after application of the product is also completely eliminated.

DETAILED DESCRIPTION OF THE INVENTION

The present invention therefore relates to preparations for treating keratinous fibers, in particular human hair, for spraying in the form of an aerosol spray, characterized in that they contain at least one wax with a melting point in a range of 40° C. to 90° C.

at least one emulsifier and at least one propellant

The first essential component of the preparations according to the invention is a wax with a melting point in a range of 40 to 90° C. In principle any physiologically acceptable waxes may be used which melt in the above-mentioned temperature range and satisfy the general definition for waxes as detailed, for example, in Ullmans Encyklopädie der technischen Chemie, 4th Edition, Vol. 24, page 3, left-hand column.

However, the waxes are preferably selected from vegetable, animal and mineral waxes, preferred waxes having a melting point in the range of 50° to 85° C., in particular 60° C. to 75° C.

Combinations of common types of wax are found in known chemical dictionaries, for example Ullmann's above-mentioned encyclopedia.

According to the invention, particularly preferred waxes include beeswax (Cera Alba), carnauba wax, candelilla wax, montan wax, microcrystalline waxes (microcrystalline paraffins) and cetyl palmitate.

The teaching according to the invention also covers the combined use of a plurality of waxes. An addition of a small amount of carnauba wax may thus be used to increase the melting and dropping point of another wax and to reduce its tackiness. A number of wax mixtures, optionally mixed with further additives, are also commercially available. Waxes known by the names "Spezialwachs 7686 OE" (a mixture of cetyl palmitate, beeswax, microcrystalline wax and polyethylene with a melting range of 73 to 75° C., produced by Kahl & Co.), Polywax® GP200 (a mixture of stearyl alcohol and polyglycol distearate with a melting point of 47 to 51° C., produced by Croda) and "Weichceresin® FL 400" (a Vaseline/Vaseline oil/wax mixture with a melting point of 50 to 54° C., produced by Parafluid Mineralölgesellschaft) are examples of preferably used mixtures according to the invention.

Apart from the compounds conventionally defined as waxes (see above), so-called "liquid waxes", for example jojoba oil, may also be used in a specific embodiment of the invention provided that the melting point of this "wax mixture" is not less than 40° C.

The preparations according to the invention contain the waxes preferably in amounts of 1.5 to 60% by weight, based on the total preparation. Amounts of 5 to 40% by weight, in particular 10 to 25% by weight, are particularly preferred.

The preparations according to the invention contain at least one emulsifier as the second essential component. Examples of possible emulsifiers include, in principle, both anionic and ampholytic, zwitterionic, cationic and nonionic surface-active compounds which are suitable for use on the human body. The use of anionic and nonionic surface-active compounds is preferred according to the invention.

Anionic surface-active compounds are characterized by a water-solubilizing anionic group, for example a carboxylate, sulfate, sulfonate or phosphate group and a lipophilic alkyl group containing about 10 to 22 carbon atoms. Glycol or polyglycol ether groups, ester, ether and amide groups and hydroxyl groups may also be contained in the molecule.

Examples of suitable anionic surface-active compounds, each in the form of sodium, potassium, magnesium and ammonium and mono-, di- and trialkanol ammonium salts containing 2 or 3 carbon atoms in the alkanol group, include linear fatty acids (soaps), ether carboxylic acids of the formula R—O—(CH$_2$—CH$_2$O)$_x$—CH$_2$—COOH, in which R is a linear alkyl group containing 10 to 22 carbon atoms and x=0 or 1 to 16, amide ether carboxylates of the formula [R—NH(—CH$_2$—CH$_2$—O)$_n$—CH$_2$—COO]$_m$Z, in which R represents a linear or branched, saturated or unsaturated acyl radical containing 2 to 29 carbon atoms, n represents integers from 1 to 10, m represents the numbers 1 or 2 and Z is a cation from the group comprising alkali or alkaline-earth metals, acyl sarcosides, acyl taurides, acyl isethionates, sulfosuccinic acid mono- and dialkyl esters, sulfosuccinic acid monoalkyl polyoxyethyl esters, linear alkane sulfonates, linear alpha-olefin sulfonates, alpha-sulfofatty acid methyl esters, alkyl sulfates and alkyl polyglycol ether sulfates of the formula R—O(CH$_2$—CH$_2$O)$_x$—SO$_3$H, in which R is a preferably linear alkyl group containing 10 to 18 carbon atoms and x=0 or 1 to 12, mixtures of surface-active hydroxysulfonates, sulfated hydroxyalkyl polyethylene and/or hydroxyalkylene propylene glycol ethers, sulfonates of unsaturated fatty acids, alcohol-containing tartaric acid and citric acid esters, representing addition products of about 2 to 15 molecules of ethylene oxide and/or propylene oxide to fatty alcohols containing 8 to 22 carbon atoms, coconut monoglyceride sulfates, phosphoric acid mono-, di- and triesters of alkoxylated fatty alcohols and mixtures thereof, for example the products sold under the trade mark Hostaphat®, and esters of hydroxy-substituted bi- or tricarboxylic acids containing polyhydroxylated organic compounds selected from the group comprising etherified ($C_8$–$C_{18}$) alkyl-polysaccharides containing 1 to 6 monomeric saccharide units and etherified aliphatic ($C_6$–$C_{16}$) hydroxyalkyl polyols containing 2 to 16 hydroxyl radicals and disclosed in European Patent EP-B1-0 258 814 to which reference is expressly made.

Preferred anionic surface-active compounds are ether carboxylic acid salts and phosphate group-containing compounds, in particular the phosphoric acid mono-, di- and triesters of ethoxylated $C_{10}$–$C_{18}$, in particular $C_{12}$–$C_{14}$, fatty alcohols with degrees of ethoxylation of 2 to 10, in particular 3 to 5.

As the hydrophilic group, nonionic surface-active compounds contain, for example, a polyol group, a polyalkylene glycol ether group or a combination of polyol and polyglycol ether group. Compounds of this type are, for example, addition products of 2 to 30 mol ethylene oxide and/or 0 to 5 mol propylene oxide to linear fatty alcohols containing 8 to 22 carbon atoms, to fatty acids containing 12 to 22 carbon atoms and to alkyl phenols containing 8 to 15 carbon atoms in the alkyl group, $C_{12}$–$C_{22}$ fatty acid mono- and diesters of addition products of 1 to 30 mol ethylene oxide to glycerin, $C_8$–$C_{22}$ alkyl mono and oligoglycosides and the ethoxylated analogues thereof and addition products of 5 to 60 mol ethylene oxide to castor oil and hardened castor oil.

Preferred nonionic surface-active compounds include the addition products of alkylene oxide, in particular ethylene oxide, to fatty alcohols and fatty acids.

Substances which carry at least one quaternary ammonium group and at least one —COO$^{(-)}$— or —SO$_3^{(-)}$ group in the molecule are called zwitterionic surface-active compounds. The so-called betaines such as the N-alkyl-N,N-dimethyl ammonium glycinates, for example coconut alkyl dimethyl ammonium glycinate, N-acyl-aminopropyl-N,N-dimethyl ammonium glycinates, for example coconut acyl aminopropyl dimethyl ammonium glycinate, and 2 alkyl-3-carboxyl methyl-3-hydroxyethyl-imidazolines each containing 8 to 18 carbon atoms in the alkyl or acyl group and coconut acyl aminoethyl hydroxyethyl carboxymethyl glycinate are particularly suitable zwitterionic surfactants. The preferred zwitterionic surfactant is the fatty acid amide derivative known by the INCI name cocamidopropyl betaine.

Substances which contain at least one free amino group and at least one —COOH or —SO$_3$H group, in addition to a $C_8$–$C_{18}$ alkyl or acyl group, in the molecule and are capable of forming inner salts are understood as ampholytic surface-active compounds. Examples of suitable ampholytic surfactants include N-alkyl glycines, N-alkyl propionic acids, N-alkyl aminobutyric acids, N-alkyl iminodipropionic acids, N-hydroxyethyl-N-alkyl amidopropyl glycines, N-alkyl-taurines, N-alkyl sarcosines, 2-alkyl aminopropionic acids and alkyl aminoacetic acids each containing about 8 to 18 carbon atoms in the alkyl group. N-coconut alkyl aminopropionate, coconut acyl aminoethyl aminopropionate and $C_{12-18}$ acylsarcosine are preferred ampholytic surfactants.

Examples of cationic surface-active compounds include, in particular, quaternary ammonium compounds. Ammonium halides, in particular chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride are preferred. The readily biologically degradable quaternary ester compounds, as sold for example under the trade mark Dehyquart® range and quaternized hydrolyzed proteins and silicone compounds may also be used according to the invention.

The compounds with alkyl groups used as surfactants may be unitary substances in each case. However, it is generally preferred to start from natural vegetable and animal raw materials in the production of these materials, so substance mixtures with different alkyl chain lengths depending on the respective raw material are obtained.

In the case of the surfactants which are addition products of ethylene and/or propylene oxide to fatty alcohols or derivatives of these addition products, products with a "normal" homolog distribution as well as those with a narrowed homolog distribution may be used. "Normal" homolog distribution refers to mixtures of homologues which are obtained in the reaction of fatty alcohol and alkylene oxide using alkali metals, alkali metal hydroxides or alkali metal alkoxides as catalysts. Narrowed homolog distributions are obtained, on the other hand, when, for example, hydrotalcites, alkaline-earth metal salts of ether carboxylic acids, alkaline-earth metal oxides, hydroxides or alkoxides are used as catalysts.

The preparations according to the invention contain the emulsifiers in amounts of 0.1 to 10% by weight, based on the total preparation. Amounts of 0.5 to 5, in particular 0.7 to 3% by weight are preferred.

The third essential component of the preparations according to the invention is the propellant.

The propellant is advantageously selected in such a way that it simultaneously serves as the solvent for the wax components. The propellant may serve as the solvent for the wax components if the wax components are soluble therein to at least 1% by weight, based on the propellant at 20° C.

Preferred propellants according to the invention are alkanes containing 3 to 5 carbon atoms, such as propane, n-butane, iso-butane, n-pentane and iso-pentane; N-butane and propane are particularly preferred.

According to a preferred embodiment, the preparations according to the invention contain said alkanes or mixtures of said alkanes as the only propellant. However, the invention expressly also covers the concurrent use of a propellant of the chlorofluorocarbon type, but in particular fluorinated hydrocarbons. Dimethyl ether in amounts of less than 5%, based on the total preparation, may be contained as additional propellant in the preparations according to the invention.

The propellants are preferably contained in the preparations according to the invention in amounts of 40 to 98% by weight, based on the total preparation. Amounts of 50 to 95% by weight, in particular 60 to 90% by weight are particularly preferred.

The preparations according to the invention may consist solely of the three mentioned essential constituents. In particular, they contain the wax as the only styling component and are free of polymers, in particular polymers with a styling effect.

It has surprisingly also been found that the oil components used in shine sprays may also be incorporated into the preparations according to the invention. Therefore, an improved shine may be conferred to the hair by applying preparations according to the invention in accordance with this embodiment. Moreover, the object of providing conventional shine sprays with additional styling properties may be achieved by preparations according to this embodiment. Vegetable as well as mineral or synthetic oils may be used as the oil component.

Therefore preparations which also contain at least one oil component, selected from vegetable, mineral or synthetic oils, are a preferred embodiment of the present invention. This oil component or these oil components are advantageously contained in the preparations according to this preferred embodiment in amounts of 0.5 to 50% by weight, in particular 5 to 50% by weight, based on the total preparation. Amounts of 10 to 40% by weight may be particularly preferred.

Triglycerides and mixtures of triglycerides are generally used as natural oils. Preferred natural oils are kukuinu oil, (sweet) almond oil, walnut oil, peach kernel oil, avocado oil, tea tree oil, soya oil, sesame oil, sunflower oil, zubaki oil, evening primrose oil, rice bran oil, palm kernel oil, mango kernel oil, lady's smock oil, thistle oil, macadamia oil, grape nut oil, apricot kernel oil, babassu oil, olive oil, pumpkin oil, mallow oil, hazelnut oil, safflower oil, canola oil, sasanqua oil and shea butter. Particularly preferred according to the invention are (sweet) almond oil, avocado oil, soya oil, sesame oil, sunflower oil, palm kernel oil, mango kernel oil, macadamia oil, apricot kernel oil, olive oil, wheatgerm oil, pumpkin oil, mallow oil and hazelnut oil.

In particular, mineral oils, paraffin and isoparaffin oils as well as synthetic hydrocarbons are used as mineral oils. A synthetic hydrocarbon which may be used according to the invention is, for example, the commercially available compound 1,3-di-(2-ethyl-hexyl)-cyclohexane (Cetiol® S). According to the invention paraffin oils are the preferred mineral oils.

Suitable synthetic oils include silicone compounds, in particular dialkyl and alkylaryl siloxanes, for example dimethyl polysiloxane and methylphenyl polysiloxane, and the hydroxy-terminated, alkoxylated and quaternized analogues thereof. Examples of silicones of this type are the products sold by Dow Corning under the names DC 190, DC 200 and DC 1401 and the commercial products DC 344 and DC 345 from Dow Corning, Q2-7224 (produced by Dow Corning; a stabilized trimethylsilyl amodimethicone), Dow Corning® 929 Emulsion (containing a hydroxyl amino-modified silicone, also called an amodimethicone), SM-2059 (produced by General Electric) and SLM-55067 (produced by Wacker). According to the invention linear and cyclic alkoxylated and non-alkoxylated dialkyl siloxanes, alkyl aryl siloxanes and siloxanes with amino groups are preferred silicone compounds.

Included in the oils which may be used according to the invention are also dialkyl ethers and dialkyl carbonates.

Dialkyl ethers which may be used according to the invention are in particular di-N-alkyl ether with a total of 12 to 36 carbon atoms, in particular 12 to 24 carbon atoms, for example di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether and n-hexyl-n-undecyl ether and di-tert-butyl ether, di-isopentyl ether, di-3-ethyl decyl ether, tert-butyl-n-octyl ether, iso-pentyl-n-octyl ether and 2-methyl-pentyl-n-octyl ether. Di-n-octyl ether is commercially available under the name Cetiol® OE.

The dialkyl carbonates which may be used according to the invention may be obtained by complete transesterification of low-molecular dialkyl carbonates, for example dimethyl carbonate or diethyl carbonate, with for example fatty alcohols containing 6 to 22 carbon atoms or the ethylene oxides and/or propyleneoxide addition products thereof. The symmetrical transesterification product di-n-octyl carbonate which may be obtained by transesterification with n-octanol (capryl alcohol) and is sold under the trade mark Cetiol® CC is particularly suitable according to the invention. Further dialkyl carbonates which may be used according to the invention have branched alkyl groups. An industrially available product of this type is, for example, di-(2-hexyl decyl)-carbonate which is obtained by transesterification of diethyl carbonate with 2-hexyldecanol, a Guerbet alcohol and also called a "Guerbet carbonate". A further preferred dialkyl carbonate with branched alkyl chains is di-(2-ethylhexyl) carbonate.

Although liquid oils are generally used at room temperature, i.e. at 25° C., the invention nevertheless also covers the use of mixtures of liquid and solid oil components, if these mixtures are liquid at room temperature.

In the preparations according to the invention of this preferred embodiment the proportion of wax components and oil components is not subject to any fundamental restrictions. The content of wax components, based on the total of wax and oil components, is generally in the range of 0.5 to 99.5% by weight, in particular in the range of 10 to 90% by weight. Preparations in which this wax content is in the range of 40 to 75% by weight are distinguished by particularly excellent properties.

The propellant content in the preparations according to this preferred embodiment is preferably 20 to 98% by weight, in particular 40 to 90% by weight and particularly preferably 50 to 80% by weight, based on the total preparation.

It has also been found that, when using silicone oils of the linear dialkyl siloxane type, the increase in shine on the hair is achieved without the characteristics of the wax components changing to a noticeable extent. On the other hand, when using paraffin oils, silicone oils of the cyclic dialkyl siloxane type and vegetable oils, a conditioning effect was noticed with respect to the wax components. Therefore the person skilled in the art has the possibility of using the oil component not only to increase the shine effect, but also to purposefully influence the properties of the wax component.

The preparations according to the invention generally contain further components which are conventional for the corresponding products. These further components include, in particular, perfume oils oil-soluble vitamins soluble UV filters dyes for coloring the preparation oil-soluble or oil-dispersible direct dyes color pigments preservatives.

Oil-soluble vitamins which are preferred according to the invention belong to groups A, D and E. The group of substances known as vitamin A includes retinol (vitamin $A_1$) and 3,4-didehydroretinol (vitamin $A_2$). β-carotene is the provitamin of retinol. Examples of the vitamin A component according to the invention include vitamin A acid and the esters thereof, vitamin A aldehyde and vitamin A alcohol and the esters thereof such as palmitate and acetate.

Vitamin E (tocopherols, in particular α-tocopherol). Tocopherol and its derivatives including, in particular, esters such as acetate, nicotinate, phosphate and succinate are preferably contained in the agents according to the invention in amounts of 0.05 to 1% by weight, based on the total agent.

Soluble UV filters are a further optional component. UV filters which are soluble in the preparations according to the invention in amounts of at least 0.1% by weight, based on the total preparation, are soluble in the sense of the invention. UV filters of this type may be selected, for example, from substituted benzophenones, p-aminobenzoic acid esters, diphenyl acrylic acid esters, cinnamic acid esters, salicylic acid esters, benzimidazoles and o-aminobenzoic acid esters.

Examples of UV filters which may be used according to the invention include 4-aminobenzoic acid, N,N,N-trimethyl-4-(2-oxoborn-3-ylidene methyl)aniline methyl sulfate, 3,3,5-trimethyl-cyclohexyl salicylate (Homosalate), 2-hydroxy-4-methoxy-benzophenone (Benzophenone-3; Uvinul® M 40, Uvasorb® MET, Neoheliopan® BB, Eusolex® 4360), 1-(4-tert.-butylphenyl)-3-(4-methoxyphenyl)-propane-1,3-dione (Butyl methoxydibenzoylmethane; Parsol® 1789, Eusolex® 9020), ethoxylated 4-aminobenzoic acid ethyl ester (PEG-25 PABA; Uvinul® P 25), 4-dimethyl aminobenzoic acid 2-ethylhexyl ester (Octyl Dimethyl PABA; Uvasorb® DMO, Escalol® 507, Eusolex® 6007), salicylic acid-2-ethylhexyl ester (Octyl salicylate; Escalol® 587, Neoheliopan® OS, Uvinul® O18), 4-methoxycinnamic acid isopentyl ester (Isoamyl p-Methoxycinnamate; Neoheliopan® E 1000), 4-methoxycinnamic acid-2-ethylhexyl ester (Octyl Methoxycinnamate; Parsol® MCX, Escalol® 557, Neoheliopan® AV), 3-(4'-methyl benzylidene)-D,L-camphor (4-Methylbenzylidene camphor; Parsol® 5000, Eusolex® 6300), 3-benzylidene camphor (3-Benzylidene camphor), 4-isopropyl benzyl salicylate, 2,4,6-trianilino-(p-carbo-2'-ethylhexyl-1'-oxy)-1,3,5-triazine, 3-imidazol-4-yl-acrylic acid ethyl ester, polymers of N-{(2 and 4)-[2-oxoborn-3-ylidenemethyl]benzyl}-acrylamide, 2,4-dihydroxybenzophenone (Benzophenone-1; Uvasorb® 20 H, Uvinul® 400), 1,1'-diphenyl acrylonitrile acid 2-ethylhexyl ester (Octocrylene; Eusolex® OCR, Neoheliopan® Type 303, Uvinul® N 539 SG), o-aminobenzoic acid menthyl ester (Menthyl Anthranilate; Neoheliopan® MA), 2,2',4,4'-tetrahydroxybenzophenone (Benzophenone-2; Uvinul® D-50), 2,2'-dihydroxy-4,4'-dimethoxy-benzophenone (Benzophenone-6) and 2-cyano-3,3-diphenyl acrylic acid-2-ethylhexyl ester. Benzophenone-3 is particularly preferred according to the invention.

Examples of suitable color pigments include pigments with the C.I. names Pigment Red: 57:1, Pigment Red 57:2, Pigment Red 172, Pigment Red 90:1, Pigment Yellow 100, Pigment Yellow 115, Pigment Red 174, Pigment Red 4, Pigment Blue 29, Pigment Violet 15, Pigment Violet 16, Pigment Red 29, Pigment Green 17, Pigment Green 18, Natural Red 4, Pigment White 6, Pigment White 14 and Pigment White 31.

With respect to further conventional ingredients, reference is expressly made to the monographs known to the person skilled in the art, for example K. Schrader, Grundlagen und Rezepturen der Kosmetika, Dr. Alfred Hüthig Verlag, Heidelberg.

The preparations according to the invention are produced and made up in the conventional manner known to the person skilled in the art. Initially, therefore, the wax components and the emulsifiers are melted and mixed. This mixture is then poured into aerosol cans in liquid form together with optional further components. After the valve has been applied, the propellant is finally added as the last component.

The invention also relates to the use of said preparations for treating keratinous fibers, in particular human hair.

The following examples are to describe the subject of the invention in more detail.

EXAMPLES

[All figures = parts by weight]

| Component | B1 | B2 | B3 | B4 | B5 | B6 |
|---|---|---|---|---|---|---|
| Carnauba wax | 1.0 | — | — | — | — | — |
| Beeswax, naturally bleached | — | 1.0 | — | — | — | — |
| Polawax® GP 200[1] | — | — | 1.0 | — | — | — |
| Candelilla wax | — | — | — | 1.0 | — | — |
| Spezialwachs 7686 OE[2] | — | — | — | — | 1.0 | 1.0 |
| Weichceresin® FL400[3] | 16.75 | 16.75 | 16.75 | 16.75 | 16.75 | 16.75 |
| Hostaphat® KL 340 N[4] | 2.0 | 2.0 | 2.0 | 2.0 | — | — |
| Hostaphat® KW 340 D[5] | — | — | — | — | 2.0 | — |
| Akypo® RLM 45 N[6] | — | — | — | — | — | 20 |
| Sunflower oil | 0.1 | 0.1 | 0.1 | 0.1 | 0.1 | 0.1 |
| Perfume oil | 0.15 | 0.15 | 0.15 | 0.15 | 0.15 | 0.15 |
| n-Butane | 80 | 80 | 80 | 80 | 80 | 80 |

| Component | B7 | B8 | B9 | B10 | B11 | B12 |
|---|---|---|---|---|---|---|
| Spezialwachs 7686 OE | 1.0 | 0.1 | 3.0 | 1.0 | 1.6 | 1.0 |
| Weichceresin® FL 400 | 6.75 | 1.54 | 50.55 | 16.85 | — | 16.75 |
| Hostaphat® KL 340 N | 2.0 | 0.2 | 6.0 | — | 0.2 | — |
| Hostaphat® KW 340 D | — | — | — | 2.0 | — | 2.0 |
| Sunflower oil | 0.1 | 0.01 | 0.3 | — | 0.05 | 0.1 |
| Neoheliopan® E 1000[7] | 5.0 | — | — | — | — | — |
| Neoheliopan® BB[8] | 5.0 | — | — | — | — | — |
| Perfume oil | 0.15 | 0.15 | 0.15 | 0.15 | 0.15 | 0.15 |
| n-Butane | 80 | 98 | 40 | 80 | 98 | — |
| n-Pentane | — | — | — | — | — | 40 |
| iso-Butane | — | — | — | — | — | 40 |

| Component | G1 | G2 | G3 | G4 | G5 | G6 |
|---|---|---|---|---|---|---|
| Spezialwachs 7686 OE | 1.0 | 1.0 | 1.0 | 1.0 | 1.0 | 1.0 |
| Weichceresin® FL 400 | 16.75 | 16.75 | 16.75 | 16.85 | 16.85 | 1.45 |
| Hostaphat® KW 340 D | 2.0 | 2.0 | 2.0 | 2.0 | 2.0 | 0.2 |
| Sunflower oil | 0.1 | 0.1 | 0.1 | 10.0 | 2.5 | 0.1 |
| Paraffin oil DAB 9 15 cP | 10.0 | — | — | — | 2.5 | — |
| Dow Corning DC 200/50 cSt[9] | — | 10.0 | — | — | 2.5 | — |
| Dow Corning DC 345[10] | — | — | 10.0 | — | 2.5 | 18.0 |
| Perfume oil | 0.15 | 0.15 | 0.15 | 0.15 | 0.15 | 0.15 |
| n-Butane | 70 | 70 | 70 | 70 | 70 | 70 |

| Component | G7 | G8 | G9 | G10 |
|---|---|---|---|---|
| Spezialwachs 7686 OE | 0.9 | 0.3 | 2.0 | 0.33 |
| Weichceresin® FL 400 | 15.05 | 4.85 | 33.75 | 5.42 |

-continued

| | | | | |
|---|---|---|---|---|
| Hostaphat ®KW 340 D | 1.8 | 0.6 | 4.0 | 0.67 |
| Sunflower oil | 0.1 | 0.1 | 0.1 | 0.1 |
| Paraffin oil DAB 9 15 cP | 2.0 | — | 40.0 | — |
| Dow Corning DC 200 Fluid 50 cSt[9] | — | — | — | 3.33 |
| Dow Corning DC 345-Fluid[10] | — | 14.0 | — | — |
| Perfume oil | 0.15 | 0.15 | 0.15 | 0.15 |
| n-Butane | 80 | 80 | 20 | 90 |

[1] Mixture of stearyl alcohol and polyethylene glycol stearate (CRODA)
[2] Mixture of cetyl palmitate, beeswax, microcrystalline wax and polyethylene (INCI-name: Cetyl Palmitate, Beeswax, Microcrystalline Wax, Polyethylene) (KAHL & CO)
[3] Vaseline/Vaseline oil/wax mixture (INCI-name: Ceresin) (PARAFLUID MINERALÖLGES.)
[4] Phosphoric acid tris($C_{12-14}$ alcohol + 4 ethylene oxide) ester (CLARIANT)
[5] Mono-di-tri-$C_{16-18}$ fatty alcohol + 4 ethylene oxide-ortho-phosphoric acid ester (CLARIANT)
[6] Lauryl alcohol + 4,5 ethylene oxide acetic acid sodium salt (about 82% active ingredient in water; INCI name: Sodium Laureth-6 Carboxylate) (CHEM-Y)
[7] 4-Methoxy cinnamic acid isoamyl ester (INCI name: Isoamyl-p-methoxycinnamate (HAARMANN & REIMER)
[8] 2-Hydroxy-4-methoxybenzophenone (INCI name: Benzophenone-3) (HAARMANN & REIMER)
[9] Polydimethyl siloxane (INCI name: Dimethicone) (DOW CORNING)
[10] Decamethyl cyclopentasiloxane (INCI name: Cyclomethicone) (DOW CORNING)

What is claimed is:

1. A method for treating keratinous fibers comprising contacting the keratinous fibers with an aerosol spray composition consisting of:
   at least one wax having a melting point range of from 40° C. to 90° C.,
   at least one emulsifier, and
   from 40 to 98%, by weight, based on the total weight of the composition, of at least one propellant,
   wherein the solubility of the wax in the propellant at 20° C. is at least 1%, by weight, based on the propellant.

2. The method of claim 1 wherein the wax is selected from the group consisting of vegetable animal and mineral waxes.

3. The method of claim 1 wherein the wax has a melting point in the range of 50° C. to 85° C.

4. The method of claim 2 wherein the wax is selected from the group consisting of beeswax, carnauba wax, candelilla wax, montane wax and cetyl palmitate.

5. The method of claim 1 wherein the emulsifier is selected from anionic and nonionic surface-active compounds.

6. The method of claim 5 wherein the anionic surface-active compound is selected from salts of either carboxylic acids and phosphate group-containing compounds.

7. The method of claim 5 wherein the nonionic surface-active compound is selected from the group consisting of addition products of alkylene oxide, fatty alcohols and fatty acids.

8. The method of claim 2 wherein the propellant is an alkane containing 3 to 5 carbon atoms.

9. The method of claim 8 wherein the alkane is selected from n-butane and propane.

10. The method of claim 2 wherein the wax is the only styling component.

11. A method for treating keratinous fibers comprising contacting the keratinous fibers with an aerosol spray composition consisting of:
    at least one wax having a melting point range of from 40° C. to 90° C.,
    at least one emulsifier,
    at least one oil component selected from the group consisting of vegetable, mineral and synthetic oils, and
    from 40 to 98%, by weight, based on the total weight of the composition, of at least one propellant,
    wherein the solubility of the wax in the propellant at 20° C. is at least 1%, by weight, based on the propellant.

12. The method of claim 11 wherein the oil component is contained in an amount of 0.5%, to 50%, by weight, based on the total composition.

13. A method for treating keratinous fibers comprising contacting the keratinous fibers with an aerosol spray composition consisting of:
    at least one wax having a melting point range of from 40° C. to 90° C.,
    at least one emulsifier,
    at least one additional component selected from the group consisting of perfume oils, oil-soluble UV-filters and dyes, and
    from 40 to 98%, by weight, based on the total weight of the composition, of at least one propellant,
    wherein the solubility of the wax in the propellant at 20° C. is at least 1%, by weight, based on the propellant.

* * * * *